(12) United States Patent
Nagai et al.

(10) Patent No.: US 6,911,326 B1
(45) Date of Patent: Jun. 28, 2005

(54) GLMU POLYPEPTIDE AND DNA ENCODING THE POLYPEPTIDE

(75) Inventors: Kazuo Nagai, Toshima-ku (JP); Masaaki Wachi, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 245 days.

(21) Appl. No.: 10/130,419

(22) PCT Filed: Nov. 17, 2000

(86) PCT No.: PCT/JP00/08120

§ 371 (c)(1),
(2), (4) Date: May 17, 2002

(87) PCT Pub. No.: WO01/38536

PCT Pub. Date: May 31, 2001

(30) Foreign Application Priority Data

Nov. 19, 1999 (JP) .......................................... 11/329648
Mar. 17, 2000 (JP) ...................................... 2000-075595

(51) Int. Cl.[7] .......................... C12P 19/26; C12N 9/10; C07H 21/04
(52) U.S. Cl. .......................... 435/84; 435/97; 435/193; 435/252.32; 435/320.1; 435/194; 536/23.2; 536/23.1; 536/23.7
(58) Field of Search .............................. 435/40, 72, 84, 435/97, 193, 194, 252.32, 320.1; 536/23.2, 23.7, 23.1

(56) References Cited

U.S. PATENT DOCUMENTS

| | | | |
|---|---|---|---|
| 6,043,071 A | 3/2000 | DeBouck et al. | ............ 435/193 |
| 6,204,042 B1 | 3/2001 | Debouck et al. | ............ 435/193 |
| 6,696,561 B1 | 2/2004 | Pompejus et al. | ......... 536/23.7 |

FOREIGN PATENT DOCUMENTS

| | | |
|---|---|---|
| EP | 0887411 A2 * | 12/1998 |
| EP | 1 108 790 | 6/2001 |
| WO | WO 97/21819 | 6/1997 |

OTHER PUBLICATIONS

Murphy, et al., Database Accession No. Z92539 (XP002281288) (1997).
Strominger, et al., "Uridine Diphosphoacetylglucosamine Pyrophosphorylase", *The Journal of Biological Chemistry*, vol. 234, No. 7 (1959), pp. 1822–1827.
Mengin–Lecreulx, et al., "Identification of the glmU Gene Encoding . . . ", *Journal of Bacteriology*, vol. 175, No. 19 (1993), pp. 6150–6157.
Hove–Jensen, "Identification of tms–26 as an Allele of the gcaD Gene . . . ", *Journal of Bacteriology*, vol. 174, No. 21 (1992), pp. 6852–6856.
Ullrich, et al., Identification of the Gonococcal glmU Gene Encoding the Enzyme . . . , *Journal of Bacteriology*, vol. 177, No. 23 (1995), pp. 6902–6909.
Mengin–Lecreulx, et al., "Copurification of Glucosamine–1–Phosphate . . . ", *Journal of Bacteriology*, vol. 176, No. 18 (1994), pp. 5788–5795.
Cole, et al., "Deciphering the biology of *Mycobacterium tuberculosis* from the complete . . . ", *Nature*, vol. 393 No. 11 (1998), pp. 537–544, Table 1 (8 pages).

* cited by examiner

*Primary Examiner*—Nashaat T. Nashed
(74) *Attorney, Agent, or Firm*—Fitzpatrick, Cella, Harper & Scinto (57) ABSTRACT

The present invention relates to a polypeptide having the activity of N-acetylglucosamine-1-phosphate uridyltransferase (hereinafter referred to as GlmU), a DNA coding for the polypeptide, a recombinant DNA containing the DNA, a transformant carrying the recombinant DNA, a method of culturing the transformant for producing the GlmU polypeptide, and a method of culturing the transformant for producing uridine 5'-diphosphate-N-acetylglucosamine.

According to the present invention, mass-scale production of the GlmU polypeptide derived from microorganisms belonging to the genus *Corynebacterium glutamicum* has been enabled by genetic recombinant technology. By using the enzyme, uridine 5'-diphosphate-N-acetylglucosamine can be produced efficiently.

22 Claims, 1 Drawing Sheet

Fig. 1

GLMU POLYPEPTIDE AND DNA ENCODING THE POLYPEPTIDE

TECHNICAL FIELD

The present invention relates to a polypeptide having the activity of N-acetylglucosamine-1-phosphate uridyltransferase (hereinafter referred to as GlmU), a DNA coding for the polypeptide, a recombinant DNA containing the DNA, a transformant carrying the recombinant DNA, a method for producing the GlmU polypeptide by using the transformant, and a method for producing uridine 5'-diphosphate-N-acetylglucosamine by using the transformant.

BACKGROUND ART

N-acetylglucosamine-1-phosphate uridyltransferase (GlmU) is an enzyme that catalyzes the production of uridine 5'-diphosphate-N-acetylglucosamine (hereinafter referred to as UDP-GlcNAc), an intermediate in biosynthesis of lipo-polysaccharides of gram-negative bacteria. Regarding GlmU polypeptides, the enzyme is purified from *Escherichia coli*, and it has been clarified that the enzyme catalyzes uridylation and also N-acetylation of glucosamine-1-phosphate [*J. Bacteriol.*, 176, 6852 (1994)].

The glmU gene is obtained from bacteria of the genus *Escherichia* [J. Bacteriol., 175, 6150(1993)], those of the genus *Bacillus* [*J. Bacteriol.*, 174, 6852 (1992)], those of the genus *Streptococcus* (Japanese Published Unexamined Patent Application No. 155582/1999), and those of the genus *Neisseria* [*J. Bacteriol.*, 177, 6902 (1995)], but the glmU gene is not identified in bacteria of the genus *Corynebacterium*.

It is reported that the N-acetylation activity of GlmU derived from *Escherichia coli* is unstable [J. Bacteriol., 176, 5788 (1994)], and the industrial application of the GlmU is problematic.

Regarding other bacteria from which the genes have been isolated, there is no description that suggests industrial production of GlmU polypeptides by the use of the gene.

DISCLOSURE OF THE INVENTION

The object of the present invention is to provide a polypeptide having GlmU activity, a DNA coding for the polypeptide, a method for producing the polypeptide having GlmU activity by using the DNA, and an industrial method for producing UDP-GlcNAc by using the polypeptide.

The present inventors have intensively studied to attain the object as mentioned above, and have found that a gene which complements the temperature sensitivity of the lysozyme-sensitive strain of *Corynebacterium glutamicum* codes for the polypeptide having GlmU activity, and on the basis of this finding, we have completed the present invention.

That is, the present invention relates to the following (1) to (13):

(1) A polypeptide comprising the amino acid sequence represented by SEQ ID NO: 1.

(2) A polypeptide comprising an amino acid sequence, in which one or more amino acids have been deleted, substituted or added in the amino acid sequence represented by SEQ ID NO: 1, and having N-acetylglucosamine-1-phosphate uridyltransferase activity.

The polypeptide comprising the amino acid sequence represented by of SEQ ID NO: 1 in which one or more amino acids have been deleted, substituted or added, and having N-acetylglucosamine-1-phosphate uridyltransferase activity is prepared according to the site-directed mutagenesis described in *Molecular Cloning, A Laboratory Manual*, Second Edition, Cold Spring Harbor Laboratory Press (1989) (this is hereinafter referred to as Molecular Cloning, 2nd Ed.), Current Protocols in Molecular Biology, John Wiley & Sons (1987–1997) (this is hereinafter referred to as *Current Protocols in Molecular Biology*), Nucleic Acids Research, 10, 6487 (1982), *Proc. Natl. Acad. Sci. USA*, 79, 6409 (1982), *Gene*, 34, 315 (1985), *Nucleic Acids Research*, 13, 4431 (1985), *Proc. Natl, Acad. Sci. USA*, 82, 488 (1985); for example, by introducing site-directed mutation into the DNA that codes for a polypeptide having the amino acid sequence represented by SEQ ID NO:1.

The number of amino acids to be deleted, substituted or added is not specifically defined, and may be on the level of deletion, substitution or addition attainable in a known method such as the site-directed mutagenesis as mentioned above, falling within a range of from 1 to tens of amino acids, preferably from 1 to 20, more preferably from 1 to 10, even more preferably from 1 to 5 amino acids.

In order that the polypeptide of the present invention has N-acetylglucosamine-1-phosphate uridyltransferase activity, it is desirable that its amino acid sequence is at least 60%, generally at least 80%, especially at least 95. % homologous to the amino acid sequence represented by SEQ ID NO: 1, calculated according to BLAST (J. Mol. Biol., 215, 403 (1990) or FASTA [*Methods in Enzymology*, 183, 63–98 (1990)].

However, the polypeptide of the present invention does not include known ones.

(3) A DNA coding for the polypeptide of above (1) or (2).

(4) A DNA comprising the nucleotide sequence represented by SEQ ID NO:2.

(5) A DNA hybridizing with the DNA of above (3) or (4) under stringent conditions, and coding for a polypeptide having N-acetylglucosamine-1-phosphate uridyltransferase activity.

The "DNA hybridizing under stringent conditions" means that it is prepared through colony hybridization, plaque hybridization or southern hybridization using the DNA having the nucleotide sequence represented by SEQ ID NO: 2 as a probe. Concretely, for example, DNA is prepared through hybridization at 65° C. on a filter on which a colony or plaque-derived DNA is fixed, in the presence of from 0.7 to 1.0 mol/l of NaCl, followed by washing the filter at 65° C. with an SSC (saline-sodium citrate) solution of about 0.1 to 2-fold concentration (the SSC solution of 1-fold concentration comprises 150 mmol/l of sodium chloride and 15 mmol/l of sodium citrate) to thereby identify the thus-hybridized DNA.

The hybridization may be conducted according to the method described in laboratory manuals of, for example, *Molecular Cloning*, 2nd Ed.; *Current Protocols in Molecular Biology*; and *DNA Cloning* 1: Core Techniques, A Practical Approach, Second Edition, Oxford University (1995). Concretely, the hybridizable DNA is, for example, a DNA of which the nucleotide sequence is at least 60%, preferably at least 80%, more preferably at least 95% homologous to the nucleotide sequence represented by SEQ ID NO:2, calculated according to BLAST or FASTA.

However, the DNA of the present invention does not include known ones.

(6) The DNA of any one of above (3) to (5), which is derived from a microorganism belonging to the genus *Corynebacterium*.

(7) The DNA of above (6), wherein the microorganisms belonging to the genus *Corynebacterium* are those of *Corynebacterium glutamicum*.

(8) A recombinant DNA obtained by ligating any one of DNA of above (3) to (7) with a vector.

(9) A transformant obtained by introducing the recombinant DNA of above (8) into a host cell.

(10) The transformant of above (9), wherein the transformant belongs to the species *Corynebacterium glutamicum*.

(11) A transformant, *Corynebacterium glutamicum* LS6/PV11 (FERM BP-6937).

(12) A process for producing a polypeptide having N-acetylglucosamine-1-phosphate uridyltransferase activity, which comprises culturing the transformant of any one of above (9) to (11) in a medium to thereby produce and accumulate a polypeptide having N-acetylglucosamine-1-phosphate uridyltransferase activity in a culture, and recovering the polypeptide from the culture.

(13) A method for producing uridine 5'-diphosphate-N-acetylglucosamine, which comprises allowing a culture obtained by culturing the transformant of any one of above (9) to (11) in a medium or a treated product of a culture, as an enzyme source, to coexist with a substrate selected from (a) uridine 5'-triphosphate, glucosamine phosphates and acetyl coenzyme A, and (b) uridine 5'-triphosphate and N-acetylglucosamine phosphates, in an aqueous medium to thereby produce and accumulate uridine 5'-diphosphate-N-acetylglucosamine in the aqueous medium, and recovering the uridine 5'-diphosphate-N-acetylglucosamine from the aqueous medium.

(14) The method for producing uridine 5'-diphosphate-N-acetylglucosamine of above (13), wherein the glucosamine phosphate is selected from glucosamine-1-phosphate or glucosamine-6-phosphate, and the N-acetylglucosamine phosphate is selected from N-acetylglucosamine-1-phosphate or N-acetylglucosamine-6-phosphate.

The present invention is described in detail hereinafter.

(1) Preparation of DNA of the present invention:

The DNA of the present invention is obtained from microorganisms belonging to the genus *Corynebacterium*. Any of the microorganisms belonging to the genus *Corynebacterium* may be used so long as it belongs to the genus *Corynebacterium*, for example, including *Corynebacterium ammoniagenes*, *Corynebacterium callunae*, and *Corynebacterium glutamicum*. One specific example is *Corynebacterium glutamicum* ATCC13032.

Microorganisms belonging to the genus *Corynebacterium* are cultured in a known method [for example, according to the method described in *Appl. Microbiol. Biotechnol.*, 39, 318 (1993)]. After the culturing, the chromosomal DNA of the microorganisms is isolated and purified in a known method [for example, according to the method described in *Current Protocols in Molecular Biology*, or *Agric. Biol. Chem.*, 49, 2925 (1885)].

The resulting chromosomal DNA is digested with suitable restriction enzymes, and the DNA fragment is inserted into a vector for *Corynebacterium* in a known method, for example, according to the description given in Molecular Cloning, 2nd Ed., to construct a recombinant DNA.

Any vector can be used so long as it is autonomously replicable in microorganisms belonging to the genus *Corynebacterium*, including, for example, pCG1 (Japanese Published Unexamined Patent Application No. 134500/1982), pCG2 (Japanese Published Unexamined Patent Application No. 35197/1983), pCG4, pCG11 (both in Japanese Published Unexamined Patent Application No. 183799/1982), pCE53, pCB101 (both in Japanese Published Unexamined Patent Application No. 105999/1993), pCE51, pCE52, pCE53 [all in *Mol. Gen. Genet.*, 196, 175 (1984)], pAJ1844 (Japanese Published Unexamined Patent Application No. 21619/1983), pHK4 (Japanese Published Unexamined Patent Application No. 20399/1995), pHK1519 [*Agric. Biol. Chem.*, 48, 2901 (1985)], pCV35, pECM1 [both in *J. Bacteriol.* 172, 1663 (1990)], and pC2 [*Plasmid*, 36, 62 (1996)].

The recombinant DNA constructed as above is introduced into lysozyme-sensitive microorganisms of the species *Corynebacterium glutamicum*. As the lysozyme-sensitive microorganisms of the species *Corynebacterium glutamicum*, any of wild type strains or mutant strains can be used, so long as it belongs to the species *Corynebacterium glutamicum* and is sensitive to lysozyme. In general, the growth of most of wild type strains is not influenced at all by existence of lysozyme at a concentration of 100 $\mu$g/ml in a culture medium. Therefore, lysozyme-sensitive mutants are preferred for use herein.

In the present invention, the lysozyme-sensitive microorganisms mean microorganisms of which the growth is inhibited when a low concentration, at most 50 $\mu$g/ml of lysozyme exists in a culture medium.

The lysozyme-sensitive microorganisms can be derived, as a mutant, from a parent strain, of the species *Corynebacterium glutamicum* according to a known method (Japanese Published Examined Application Nos. 49038/1987, 29555/1989, Japanese Published Unexamined Patent Application No. 56678/1983). The mutant includes, for example, *Corynebacterium glutamicum* ATCC31834 derived from *Corynebacterium glutamicum* ATCC31833 (Japanese Published Unexamined Patent Application No. 56678/1983), and *Corynebacterium glutamicum* LS6 mentioned below, derived from *Corynebacterium glutamicum* ATCC13032.

Some lysozyme-sensitive microorganisms are also sensitive to a temperature in their growth. The lysozyme-sensitive and temperature-sensitive (hereinafter referred to as lysozyme/temperature-sensitive) microorganisms cannot grow at high temperatures (for example, at from 34 to 39° C.) even when no lysozyme exists in a culture medium.

The mutant of this type includes, for example, *Corynebacterium glutamicum* LS6 mentioned below, derived from *Corynebacterium glutamicum* ATCC13032.

The DNA of the present invention can be obtained as a DNA that complements the temperature sensitivity of the lysozyme/temperature-sensitive strain.

That is, the DNA obtained as above is ligated with a vector, and the lysozyme/temperature-sensitive strain is transformed with the DNA-ligated vector. The transformant is cultured in a lysozyme-free medium at a temperature at which the lysozyme-sensitive microorganisms could not grow, for example, at 34 to 39° C., preferably at 36 to 38° C. The strain capable of growing in the temperature condition is selected as that having the intended DNA, and the DNA is obtained from the strain.

The method is described in detail below.

For the recombinant DNA introduction, any method of introducing a DNA into the above-mentioned lysozyme/temperature-sensitive microorganisms can be employed. For example, the protoplast method [Japanese Published Unexamined Patent Application Nos. 186492/1982 and 56678/1983, *J. Bacteriol.*, 159, 306 (1984)], and the electroporation method (Japanese Published Unexamined Patent Application No. 207791/1990) are mentioned.

Alternatively, using a chromosomal DNA library of lysozyme-insensitive strains belonging to the genus *Coryne-* bacterium as constructed in *Escherichia coli*, the recombinant DNA may be introduced into the lysozyme/temperature-sensitive strain of *Corynebacterium glutamicum* through bacterial conjugation transfer from *Escherichia coli* in the library according to a known method [J. Bacteriol., 172, 1663 (1990), J. Bacteriol., 178, 5768 (1996)].

The lysozyme/temperature-sensitive strain of *Corynebacterium glutamicum* with the recombinant DNA introduced thereinto is cultured, for example, in an LB medium [10 g/l of bactotryptone (produced by Difco), 5 g/l of yeast extract (produced by Difco), 5 g/l of sodium chloride (pH 7.2)] at a high temperature (34 to 39° C.) for 24 to 72 hours. After culturing, the strain having grown in the medium is selected as that having the intended DNA.

The DNA thus obtained is, directly as it is or after digestion with suitable restriction enzymes, ligated with a vector in an ordinary manner, and the nucleotide sequence of the DNA is determined in an ordinary sequencing method, for example, according to a dideoxy method using a DNA sequencer of 373A Model (produced by Parkin Elmer) [Proc. Natl. Acad. Sci. USA, 74, 5463 (1977)].

The vector to be ligated with the DNA includes, for example, pBluescript KS(+) (produced by Stratagene), pDIRECT [Nucleic Acids Research, 18, 6069(1990)], pCR-Script Amp SK(+) (produced by Stratagene), pT7Blue (produced by Novagen), pCR II (produced by Invitrogen), pCR-TRAP (produced by Gene Hunter) and pNoTAT7 (produced by 5 Prime→3 Prime).

The DNA comprising a novel nucleotide sequence obtained in the manner as above, for example, the DNA having the sequence represented by SEQ ID NO: 2 is mentioned.

The DNA comprising the nucleotide sequence represented by SEQ ID NO: 2 codes for the polypeptide having the amino acid sequence represented by SEQ ID NO: 1.

The strain that carries the plasmid comprising the DNA comprising the nucleotide sequence represented by SEQ ID NO: 2 includes, for example, *Corynebacterium glutamicum* LS6/pV5, and *Corynebacterium glutamicum* LS6/pV11.

Using a primer prepared on the basis of the nucleotide sequence determined as above and using the chromosomal DNA as a template, the intended DNA can be obtained through the PCR method [*PCR Protocols*, Academic Press (1990)].

Further, on the basis of the determined DNA sequence, the intended DNA can also be prepared through chemical synthesis in a DNA synthesizer, such as Perceptive Biosystems' 8905 Model. (2) Preparation of Polypeptide of the present invention:

The polypeptide of the present invention can be produced by expressing the DNA of the present invention in host cells, according to the method described in *Molecular Cloning*, 2nd Ed., and *Current Protocols in Molecular Biology*, for example, according to the method mentioned below.

That is, a recombinant DNA is constructed by ligating the DNA of the present invention downstream the promoter of a suitable expression vector, and this is introduced into host cells suitable for the expression vector, whereby a transformant being capable of producing the polypeptide of the present invention can be obtained. Any host cell can be used so long as it is capable of expressing the intended gene, including, for example, bacteria, yeast cells, animal cells, insect cells and plant cells. The expression vector needs to be capable of replicating in host cells or being integrated with the chromosome therein, and need to have a promoter in the site in which the DNA coding for the polypeptide of the present invention can be transcribed.

In case where prokaryotes such as bacteria are used for host cells, it is desirable that the recombinant DNA containing the DNA coding for the polypeptide of the present invention is self-replicable in prokaryotes and comprises a promoter, a ribosome-binding sequence, the DNA that codes for the polypeptide of the present invention and a transcription termination sequence. If desired, the recombinant DNA may contain a gene for regulating the promoter.

The expression vector includes, for example, pC2 [*Plasmid*, 36, 62 (1996)], pBTrp2, pBTac1, pBTac2 (all commercial products of Boehringer Mannheim), pKK233-2 (produced by Pharmacia), pSE280 (produced by Invitrogen), pGEMEX-1 (produced by Promega), pQE-8 (produced by QIAGEN), pKYP10(Japanese Published Unexamined Patent Application No. 110600/1983), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (produced by Stratagene), pTrs30 [prepared from *Escherichia coli* JM109/pTrS30 (FERMBP-5407)], pTrs32 [prepared from *Escherichia coli* JM109/pTrS32 (FERM BP-5408)], pGHA2 [prepared from *Escherichia coli* IGHA2 (FERM B-400), Japanese Published Unexamined Patent Application No. 221091/1985], pGKA2 [prepared from *Escherichia coli* IGKA2 (FERM BP-6798), Japanese Published Unexamined Patent Application No. 221091/1985], pTerm2 (U.S. Pat. No. 4,686,191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (produced by Pharmacia), and pET system (produced by Novagen).

For host microorganisms belonging to the genus *Corynebacterium*, vectors such as pCG1, pCG2, pCG4, pCG 11, pCE53, pCB101, pCE51, pCE52, pCE53, pAJ1844, pHK4, pHM1519, pCV35 and pECM1 are further usable in addition to the vectors mentioned above.

As the promoter to be used herein, any promoter can be used, so long as it is capable of being expressed in the host cells. For example, it is derived from *Escherichia coli* or phages, including trp promoter ($P_{trp}$), lac promoter, $P_L$ promoter, $P_R$ promoter and T7 promoter. Artificially-designed or modified promoters, such as a promoter of two $P_{trp}$' S linked in tandem ($P_{trp}$×2), tac promoter, lacT7 promoter, and letI promoter, can also be used.

Plasmids which are specifically so designed that the ribosome-binding sequence, Shine-Dalgarno sequence is spaced from the initiation codon by a suitable distance (e.g., by 6 to 18 bases) therein are preferred for use herein.

Some nucleotides in the part of the nucleotide sequence that codes for the polypeptide of the present invention may be substituted with any others so that the resulting codon may be the most suitable for polypeptide expression in host cells, whereby the productivity of the intended polypeptide can be increased.

The recombinant vector for use in the present invention does not always require a transcription termination sequence for expression of the DNA of the present invention. In the recombinant vector, however, it is desirable that a transcription termination sequence is just downstream the structural gene.

The host cells include microorganism belonging to the genus *Escherichia, Serratia, Bacillus, Brevibacterium, Corynebacterium, Microbacterium* and *Pseudomonas* and the like, including, for example, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli*

HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium acetoacidophilum* ATCC 13870, *Microbacterium ammoniaphilum* ATCC 15354, and *Pseudomonas* sp. D-0110.

For introducing the recombinant vector into the host cells, any method of introducing DNA thereinto can be employed. For example, the method assisted by calcium ions [*Proc. Natl. Acad. Sci. USA*, 69, 2110 (1972)], the protoplast method (Japanese Published Unexamined Patent Application No. 248394/19B8), the electroporation method (Japanese Published Unexamined Patent Application No. 207791/1990), and the methods described in Gene, 17, 107 (1982) and *Molecular & General Genetics*, 168, 111 (1979) are mentioned.

In case where yeast is used for host cells, the expression vector for this purpose includes, for example, YEp13 (ATCC 37115), YEp24 (ATCC 37051) and YCp50(ATCC 37419).

As the suitable promoter, any promoter can be used, so long as it is capable of being expressed in yeast cells, including, for example, promoters for genes participating in glycolysis such as hexosekinase, as well as PH05 promoter, PGK promoter, GAP promoter, ADH promoter, gal 1 promoter, gal 10 promoter, heat-shock polypeptide promoter, MFα1 promoter, and CUP1 promoter.

The host cells include a microorganism belonging to the genus *Saccharomyces, Kluyveromyces, Trichosporon, Schwanniomyces* and the like, including, for example, *Saccharomyces cerevisiae, Schizosaccharomyces pombe, Kluyveromyces lactis, Trichosporon pullulans* and *Schwanniomyces alluvius*.

For introducing the recombinant DNA into the host cells, any method of introducing DNA into yeast cells is employable. For example, the electroporation method [*Methods Enzymol.*, 194, 182 (1990)], the spheroplast method [*Proc. Natl. Acad. Sci. USA*, 84, 1929 (1978)1, the lithium acetate method [*J. Bacteriol.*, 153, 163 (1983)], and the method described in *Proc. Natl. Acad. Sci. USA*, 75, 1929 (1978) are mentioned.

In case where animal cells are used for host cells, the expression vector for this purpose includes, for example, pcDNAI, pcDM8 (commercially sold by Funakoshi), pAGE107 [Japanese Published Unexamined Patent Application No. 22979/1991, *Cytotechnology*, 3, 133 (1990)], pAS3-3 (Japanese Published Unexamined Patent Application No. 227075/1990), pCDM8 [*Nature*, 329, 840 (1987)], pcDNAI/Amp (produced by Invitrogen), pREP4 (produced by Invitrogen), pAGE103 [*J. Biochemistry*, 101, 1307 (1987)], and pAGE210.

As the promoter, any promoter may be used, so long as it is capable of being expressed in animal cells, including, for example, the promoter of IE (immediate early) gene of cytomegalovirus (CMV), the early promoter of SV40, the promoter of retrovirus, as well as metallothionein promoter, heat-shock promoter, and SRα promoter. The enhancer of the IE gene of human CMV may be used together with the promoter.

The host cells include, for example, Namalwa cells of human, COS cells of monkey, CHO cells of Chinese hamster, and HBT5637 cells (Japanese Published Unexamined Patent Application No. 299/1988).

For introducing the recombinant vector into the animal cells, any method of introducing DNA into animal cells is employable. For example, the electroporation method [*Cytotechnology*, 3, 133 (1990)], the calcium phosphate method (Japanese Published Unexamined Patent Application No. 227075/1990), and the lipofection method (*Proc. Natl. Acad. Sci. USA*, 84, 7413 (1987)] are mentioned.

In case where insect cells are used for host cells, the polypeptide may be expressed, for example, according to the methods described in *Current Protocols in Molecular Biology; Baculovirus Expression Vectors*, A Laboratory Manual, W. H. Freeman and Company, New York (1992); and *Bio/Technology*, 6, 47 (1988).

That is, a recombinant gene introduction vector and a Baculovirus are simultaneously introduced into insect cells to obtain a recombinant virus in a culture supernatant of the insect cell, and then insect cells are infected with the recombinant virus so as to express the polypeptide.

The gene introduction vector to be used in the method includes, for example, pVL1392, pVL1393 and pBlueBacIII (all produced by Invitrogen).

An example of the Baculovirus is, for example, *Autographa californica* nuclear polyhedrosis virus that infects armyworms of *Barathra*.

The insect cells include, for example, *Spodoptera frugiperda* oocytes, Sf9, Sf21 [*Baculovirus Expression Vectors, A Laboratory Manual, W. H. Freeman and Company, New York* (1992)], and *Trichoplusia ni* oocytes, High 5 (produced by Invitrogen).

For simultaneously introducing the recombinant gene introduction vector and the Baculovirus into insect cells to prepare a recombinant virus, for example, the calcium phosphate method (Japanese Published Unexamined Patent Application No. 227075/1990) and the lipofection method [*Proc. Natl. Acad. Sci. USA*, 84, 7413 (1987)] are employable.

In case where plant cells are used for host cells, the expression vector for the purpose includes, for example, Ti plasmid and tobacco mosaic virus vector.

As the promoter, any promoter can be used so long as it is capable of being expressed in plant cells, including, for example, 35S promoter of cauliflower mosaic virus (CaMV), and rice actin 1 promoter.

The plant cells for host cells include, for example, those of tobacco, potato, tomato, carrot, soybean, rape, alfalfa, rice, wheat, and barley.

For introducing the recombinant DNA into such plant cells, any method of introducing DNA thereinto is employable, including, for example, the method by using *Agrobacterium* (Japanese Published Unexamined Patent Application Nos. 140885/1984 and 70080/1985, w094/00977), the electroporation method (Japanese Published Unexamined Patent Application No. 251887/1985), and the method by using a particle gun (gene gun) (Japanese Published Examined Patent No. 2,606,856, 2,517,813).

The gene expression may be conducted in a mode of direct expression, or in a mode of secretion production or fused protein expression according to the method described in Molecular Cloning, 2nd Ed.

In case where the gene is expressed in yeast cells, animal cells, insect cells or plant cells, it gives a polypeptide with a saccharide or sugar chain added thereto.

The transformant prepared in the manner as above is cultured in a medium, and the polypeptide of the present invention is produced and accumulated in a culture, and recovered from the culture. For culturing the transformant of the present invention in a medium, any method for culturing a host cell as generally used in the art is employable.

In case where the transformant of the present invention is prepared by the use of bacteria such as *Escherichia coli* or eukaryotic host cells including, for example, yeast cells, the medium in which the transformant is cultured may be any natural or synthetic medium containing carbon sources, nitrogen sources and inorganic salts which can be assimilated by the transformant and in which the transformant can be efficiently cultured.

The carbon sources may be any ones which can be assimilated by the transformant, including, for example, carbohydrates such as glucose, fructose, sucrose, molasses containing them, starch or starch hydrolyzates; organic acids such as acetic acid and propionic acid; and alcohols such as ethanol and propanol.

The nitrogen sources include, for example, ammonia, ammonium salts of inorganic acids and organic acids, such as ammonium chloride, ammonium sulfate, ammonium acetate, ammonium phosphate; other nitrogen-containing compounds; and peptone, meat extracts, yeast extracts, corn steep liquor, casein hydrolyzates, soy bean meal, soy bean meal hydrolyzates, various cells obtained by fermentation and their digested products.

The inorganic salts include, for example, potassium dihydrogenphosphate, dipotassium hydrogenphosphate, magnesium phosphate, magnesium sulfate, sodium chloride, ferrous sulfate, manganese sulfate, copper sulfate, and calcium carbonate.

Culturing the transformant in the medium is generally conducted under aerobic conditions, for example, by shaking culture or submerged spinner culture under aeration. The culturing temperature is preferably from 15 to 40° C., and the culturing period is generally from 16 hours to 7 days. Preferably, the pH of the culture is from 3.0 to 9.0. For the pH control, any of inorganic or organic acids, alkali solutions, urea, calcium carbonate or ammonia or the like may be used.

If desired, antibiotics such as ampicillin, tetracycline and kanamycin may be added to the medium in which the transformant is cultured.

In case where microorganisms transformed with a recombinant vector having an inducible promoter are cultured, an inducer may be added to the medium, if desired. For example, when microorganisms transformed with a recombinant vector having lac promoter are cultured, isopropyl-β-D-thiogalactopyranoside may be added to the medium; and when microorganisms transformed with a recombinant vector having trp promoter are cultured, indole-acrylic acid may be added to the medium.

The medium in which the transformant prepared by using animal cells as a host cell is cultured may be any ordinary one, including, for example, RPMI1640 medium [*The Journal of the American Medical Association,* 199, 519 (1967)], Eagle's MEM medium [*Science,* 122, 501 (1952)], Dulbecco's modified MEM medium [*Virology,* 8, 396(1959)], 199 medium [*Proceeding of the Society for the Biological Medicine,* 73, 1 (1950)], and those media with fetal calf serum therein.

Culturing the transformant in the medium is conducted generally at pH 6 to 8, at 30 to 40° C. in the presence of 5% $CO_2$ for 1 to 7 days.

If desired, antibiotics such as ampicillin and tetracycline may be added to the medium in which the transformant is cultured.

The medium in which the transformant prepared by using insect cells as a host cell is cultured may be any ordinary one, including, for example, TNM-FH medium (produced by PharMingen), Sf-900 II SFM medium (produced by Life Technologies), ExCell 400, ExCell 405 [both produced by JRH Biosciences] and Grace's Insect Medium [*Nature,* 195, 788 (1962)].

Culturing the transformant in the medium is conducted generally at pH 6 to 7, at 25 to 30° C. for 1 to 5 days.

If desired, antibiotics such as gentamycin may be added to the medium in which the transformant is cultured.

The transformant cells prepared by using plant cells as a host cell may be cultured as they are, or after differentiated into plant cells or organs. The medium in which the transformant is cultured may be any ordinary one, including, for example, Murashige & Skoog (MS) medium, White medium, and those media with a plant hormone such as auxin or cytokinin therein.

Culturing the transformant in the medium is conducted generally at pH 5 to 9, at 20 to 40° C. for 3 to 60 days.

If desired, antibiotics such as kanamycin and hygromycin may be added to the medium in which the transformant is cultured.

As described above, the transformant derived from microorganisms, animal cells or plant cells carrying a recombinant vector ligated with the DNA coding for the polypeptide of the present invention is cultured in an ordinary manner to thereby produce and accumulate the polypeptide, and the polypeptide is recovered from the culture.

The gene expression may be conducted in a mode of direct expression, or in a mode of secretion production or fused polypeptide expression according to the method described in *Molecular Cloning,* 2nd Ed.

The method for producing the polypeptide of the present invention includes intracellular production, extracellular secretion or production on cell outer membrane of host cells, and the method can be selected depending on the host cells used or on alteration the structure of the polypeptide to be produced.

In case where the polypeptide of the present invention is produced inside host cells or on the outer membrane of host cells, it can be secreted in the extracellular portion from the host cells, according to the method of Paulson, et al. [*J. Biol. Chem.,* 264, 17619 (1989)], the method of Lowe, et al. [*Proc. Natl. Acad. Sci., USA,* 86, 8227 (1989), *Genes Develop.,* 4, 1288 (1990)] or the methods described in Japanese Published Unexamined Patent Application No. 336963/1993 and WO94/23021.

That is, the polypeptide of the present invention can be secreted in the extracellular portion from the host cells, by expressing it in the form of a polypeptide containing the active site of the polypeptide of the present invention and having a signal peptide upstream it, according to gene recombination technology.

The yield of the polypeptide to be produced can be increased in a gene amplification system using a dihydrofolate reductase gene or the like, according to the method described in Japanese Published Unexamined Patent Application No. 227075/1990.

In addition, the gene-introduced animal or plant cells may be re-differentiated to construct gene-introduced animal individuals (transgenic non-human animals) or plant individuals (transgenic plants). Using these individuals, the polypeptide of the present invention may be produced.

In case where the transformant is an animal individual or plant individual, it may be raised or cultivated in an ordinary manner to thereby produce and accumulate the intended polypeptide therein, and the polypeptide is recovered from the animal or plant individual.

For producing the polypeptide of the present invention in animal individuals, for example, an animal is transformed with the gene coding for the polypeptide, and the polypeptide is produced in the transformant animal according to known methods [*American Journal of Clinical Nutrition*, 63, 639S (1996), *American Journal of Clinical Nutrition*, 63, 627S (1996), Bio/Technology, 9, 830 (1991)].

For animal individuals, for example, the transgenic non-human animals carrying the DNA coding for the polypeptide of the present invention are raised to thereby produce and accumulate the polypeptide in the animals, and the polypeptide is recovered from the animals. The site of the animals in which the polypeptide is produced and accumulate is, for example, milk (Japanese Published Unexamined Patent Application No. 309192/1988), eggs of the animals, and the like. The promoter to be used may be any promoter which is capable of being expressed in animals. For example, mammary gland cell-specific promoters such as α-casein promoter, β-casein promoter, ⊕-lactoglobulin promoter, whey acidic protein promoter, and the like, are preferably used.

For producing the polypeptide of the present invention in plant individuals, for example, a transgenic plant carrying the DNA coding for the polypeptide of the present invention is cultivated in known methods [*Tissue Culture*, 20 (1994), *Tissue Culture*, 21 (1995), *Trends in Biotechnology*, 15, 45 (1997)] to thereby produce and accumulate the polypeptide in the plant, and the polypeptide is recovered from the plant.

For isolating and purifying the polypeptide having been expressed according to the methods mentioned above, from the transformant cultures, any ordinary enzyme isolation and purification method is employable.

For example, when the polypeptide of the present invention is expressed in soluble forms inside the transformant cells, the cells are, after cultured, recovered from the culture by centrifuging the culture, then suspended in an aqueous buffer, and disrupted with an ultrasonic disrupter, French Press, Manton-Gaulin homogenizer, Dynomill or the like to obtain a cell-free extract. The cell-free extract is centrifuged, and the resulting supernatant is purified through ordinary enzyme isolation and purification methods. Specifically, for example, the supernatant is purified through solvent extraction, salting-out or desalting with sulfate ammonium or the like, precipitation with organic solvent, anion-exchange chromatography on resin such as diethylaminoethyl (DEAE)-Sepharose or DIAION HPA-75 (produced by Mitsubishi Chemical Industries), or the like, cation-exchange chromatography on resin such as S-Sepharose FF (produced by Pharmacia), hydrophobic chromatography on resin such as butyl Sepharose or phenyl Sepharose, gel filtration through molecular sieve, affinity chromatography, chromatofocusing, or electrophoresis such as isoelectric focusing, or the like. The purification methods may be used either singly or as combined to obtain the intended pure product.

In case where the polypeptide is expressed as an inclusion body in the cells, the cells are similarly recovered, disrupted and centrifuged to give a precipitated fraction that contains the inclusion body of the polypeptide. The thus-recovered inclusion body of the polypeptide is solubilized with a protein denaturing agent. The solubilized solution is then diluted or dialyzed to thereby lower the concentration of the protein denaturing agent in the solution, in which concentration, the protein may not be denatured. Through the process, the solubilized polypeptide is renatured to have its own normal tertiary structure. After thus processed, the polypeptide is purified through the same isolation and purification as above to be a pure product.

In case where the polypeptide of the present invention or the polypeptide derivative with a sugar chain added thereto is secreted from the cells, the polypeptide or the sugar chain-added polypeptide derivative can be recovered in the culture supernatant. Specifically, the culture is centrifuged in the same manner as above to obtain the culture supernatant containing a soluble fraction, and the fraction is purified through the same isolation and purification as above to obtain a pure polypeptide product.

As the polypeptide thus obtained in the manner as above, for example, the polypeptide having the amino acid sequence represented by SEQ ID NO:1 is mentioned.

The polypeptide of the present invention can be produced through chemical synthesis of, for example, an Fmoc method (fluorenylmethyloxycarbonyl method) or a tBoc method (t-butyloxycarbonyl method). It may also be produced through chemical synthesis using peptide synthesizers such as those produced by Advanced ChemTech, Parkin-Elmer, Pharmacia, Protein Technology Instrument, Synthecell-vega, PerSeptive, and Shimadzu.

(3) Preparation of UDP-GlcNAc:

Using the transformant culture obtained in the above (2) or its treated product obtained by treating the culture in various methods, as an enzyme source, and putting the enzyme source and a substrate for it in an aqueous medium, UDP-GlcNAc can be produced in the aqueous medium.

The treated product of the transformant culture includes, for example, concentrated products of the culture, dried products of the culture, cells obtained by centrifuging the culture, dried products of the cells, lyophilized products of the cells, surfactant-treated products of the cells, ultrasonically-treated products of the cells, mechanically-disrupted products of the cells, solvent-treated products of the cells, enzyme-treated products of the cells, polypeptide fractions from the cells, immobilized products of the cells, and enzyme products extracted from the cells.

The concentration of the enzyme source to be used in producing UDP-GlcNAc may be from 1 to 500 g wet cells/l, but preferably from 10 to 300 g wet cells/l, in terms of the weight of the cells (wet cells) just after centrifugation of the culture.

The aqueous medium to be used in producing the UDP-GlcNAc includes, for example, water; buffers such as phosphate, carbonate, acetate, borate, citrate, Tris; alcohols such as methanol, ethanol; esters such as ethyl acetate; ketones such as acetone; and amides such as acetamide. The culture of the microorganisms serving as the enzyme source may also be used for the aqueous medium.

If desired, a surfactant or organic solvent may be added to the aqueous medium for producing UDP-GlcNAc. As the surfactant, any surfactant may be used so long as it does not inhibit with the production of UDP-GlcNAc, including, for example, nonionic surfactants such as polyoxyethylene-octadecylamine (e.g., Nymeen S-215, produced by Nippon Oil & Fats); cationic surfactants such as cetyltrimethylammonium bromide and alkyldimethylbenzylammonium chlorides (e.g., Cation F2-40E, produced by Nippon Oil & Fats); anionic surfactants such as lauroyl sarcosinate; and tertiary amines such as alkyldimethylamines (e.g., Tertiary Amine FB, produced by Nippon Oil & Fats). One or more of such surfactants may be used either singly or as combined. The surfactant concentration is generally from 0.1 to 50 g/l. The organic solvent includes, for example, xylene, toluene, aliphatic alcohols, acetone, and ethyl acetate. The solvent concentration is generally from 0.1 to 50 ml/l.

The substrate to be used in producing UDP-GlcNAc includes uridine 5'-triphosphate and glucosamine derivatives.

The glucosamine derivatives are, for example, glucosamine phosphates selected from glucosamine-1- phosphate and glucosamine-6-phosphate, or N-acetylglucosamine phosphates selected from N-acetylglucosamine-1-phosphate and N-acetylglucosamine-6-phosphate. In case where a glucosamine phosphate is used as the glucosamine derivative, acetyl coenzyme A (acetyl CoA) need to be added thereto. However, when acetyl CoA already exists in the enzyme source, it may not be added to the aqueous medium.

In case where the enzyme product obtained through cell extraction is used for the enzyme source, the glucosamine derivative to be used with the enzyme product is glucosamine-1-phosphate or N-acetylglucosamine-1-phosphate. However, when the enzyme source contains an enzyme having the activity to convert glucosamine-6-phosphate or N-acetylglucosamine-6-phosphate into glucosamine-1-phosphate or N-acetylglyucosamine-1-phsophate, glucosamine-6-phosphate or N-acetylglucosamine-6-phosphate may be used as the glucosamine derivative.

The substrate concentration may be from 0.1 to 500 mmol/l.

The reaction in the aqueous medium to produce UDP-GlcNAc is conducted at pH 5 to 10, preferably from 6 to 8, at 20 to 60° C. for 1 to 96 hours. If desired, an inorganic salt such as $MgCl_2$ may be added to the reaction mixture.

UDP-GlcNAc produced in the aqueous medium can be quantified in a known manner such as HPLC [for example, as in WO98/12343].

UDP-GlcNAc produced in the reaction mixture can be recovered in any ordinary manner using, for example, activated charcoal or ion-exchange resin.

Examples of the present invention are described below, to which, however, the present invention is not limited.

BEST MODES OF CARRYING OUT THE INVENTION

EXAMPLE 1

Preparation of Chromosomal DNA of *Corynebacterium glutamicum* ATCC 13032

*Corynebacterium glutamicum* ATCC 13032 was inoculated in 10 ml of an L' medium (1% of polypeptone, 0.5% of yeast extract, 0.5% of sodium chloride, 0.1% of glucose, 20 mg/l of thiamine hydrochloride, pH 7.2) and cultured overnight at 30° C.

After culturing, the cells were recovered from the culture through centrifugation.

The cells were washed with TE buffer [10 mmol/l of Tris-HCl, 1 mol/l of ethylenediaminetetraacetate (EDTA), pH 8.0], and suspended in 800 μl of the same buffer. 40 μl of a lysozyme solution (50 mg/ml) and 20 μl of an RNase A solution (10 mg/ml) were added to the suspension, and reacted at 37° C. for 1 hour.

20 μl of sodium dodecyl sulfate (SDS) solution (20%) was added to the reaction mixture, and reacted at 70° C. for 1 hour. 24 μl of a proteinase K solution (20 mg/ml) was added thereto and reacted at 50° C. for 1 hour. 24 μL of the proteinase K solution was further added thereto, and reacted at 50° C. for 1 hour. To the reaction solution, phenol of the same amount as that of the reaction solution was added and stirred, and then left at 4° C. overnight, whereby the DNA was extracted out in the aqueous phase, and the aqueous phase was collected.

To the aqueous phase, phenol/chloroform (1/1, vol/vol) of the same amount as that of the aqueous phase was added, stirred, and extracted for 2 hours, and the aqueous phase was recovered. To the aqueous phase, chloroform/isoamyl alcohol (24/1, vol/vol) of the same amount as that of the aqueous phase was added, stirred, and extracted for 30 minutes, and the aqueous phase was recovered. To the aqueous phase, ethanol of twice of the aqueous phase was added, and the DNA was precipitated. The resulting precipitate was dissolved in 300 μl of a TE buffer, and used as the chromosomal DNA below.

EXAMPLE 2

Separation of Temperature-Sensitivity Complementing Gene 0.5 μg of the chromosomal DNA obtained in Example 1 and 0.5 μg of a plasmid pC2 were digested with BamHI, and their fragments were ligated using a ligation kit (Takara DNA Ligation Kit ver. 2, produced by TAKARA), at 16° C. for 16 hours.

Lysozyme/temperature-sensitive *Corynebacterium glutamicum* LS6 was transformed with the ligated product by electroporation (Japanese Published Unexamined Patent Application No. 207791/1990), and the transformant was selected based on the property of the strain LS6 which is sensitive to temperature. That is, the transformant was spread on an L'-agar plate medium (prepared by adding 1.5% agar to an L'-medium) containing 5 μl/ml kanamycin, and cultured at 37° C. for 3 days.

The resulting colonies were cultured according to the method of Example 1, and the plasmid was recovered according to the method described in *Molecular Cloning*, 2nd Ed. The recovered plasmid pV5 was analyzed for its structure. It was found that the plasmid pV5 has a DNA fragment of about 7 kb derived from *Corynebacterium glutamicum* inserted into the BamHI site of the plasmid pC2.

Figure 1:
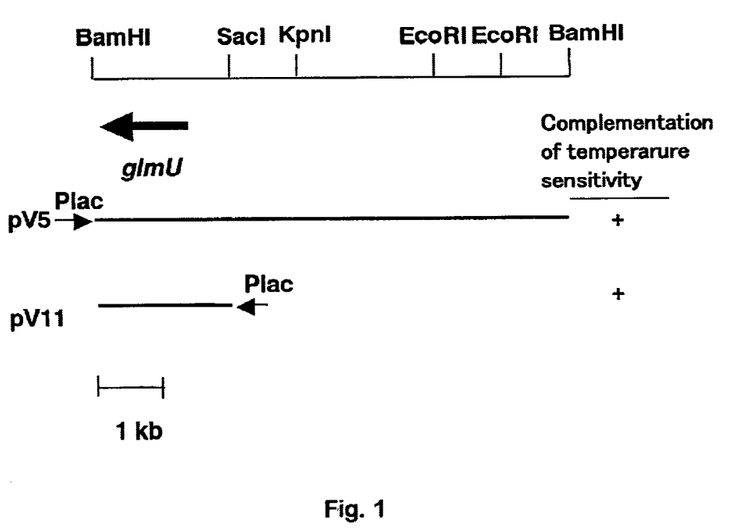
FIG. 1 shows the result of a temperature-sensitivity complementation test with *Corynebacterium glutamicum* LS6, in which various deletion plasmids having a ligated DNA fragment of about 7 kb were prepared and tested. "Plac" indicates the site of the lactose promoter existing in the vector pC2. "+"indicates that the plasmid complemented the temperature sensitivity of the transformant. An outline of the restriction enzyme map of the DNA fragment insert of about 7 kb, and the site and the direction of the glmU gene are shown in FIG. 1.

Various deletion plasmids were obtained by using the DNA fragment of about 7 kb inserted into the plasmid pV5, in an ordinary manner. With each deletion plasmid, *Corynebacterium glutamicum* LS6 was transformed, and the temperature sensitivity of the transformant was investigated. It was found that a BamHI-SacI fragment of 2.3 kb was required to complement the temperature sensitivity (FIG. 1).

The nucleotide sequence of the BamHI-SacI fragment of 2.3 kb was determined, and it was confirmed that an open reading frame (ORF) of 1455 bp having the nucleotide sequence represented by SEQ ID NO: 2 and coding for the amino acid sequence of 485 amino acid residues represented by SEQ ID NO; 1 exists in the region of this fragment.

The amino acid sequence homology of the DNA to different amino acid sequences was studied according to BLAST P2.0.10. As a result, the amino acid sequence represented by SEQ ID NO: 1 was 40% homologous to the amino acid sequence of GlmU derived from *Escherichia coli* heretofore reported [*J. Biochem.*, 115, 965 (1994)], and was 40% homologous to the amino acid sequence of GlmU derived from *Bacillus subtilis* [*J. Gen. icrobiol.*, 139, 3185 (1993)].

The nucleotide sequence homology of the DNA to different nucleotide sequences was also studied according to BLAST N2.0.10. As a result, no homology of the nucleotide sequence represented by SEQ ID NO: 2 that codes for the amino acid sequence was found to any others.

*Corynebacterium glutamicum* LS6/pV11 that contains the plasmid pv11 having the BamHI-SacI fragment of 2.3 kb was deposited as FERM BP-6937 on Nov. 12, 1999 with the International Patent Organism Depositary, National Institute of advanced Industrial Science and Technology (AIST Tsukuba Central 6, 1-1, Higashi 1-Chome Tsukuba-shi, Ibaragi-ken 305–8566 Japan) [National Institute of Bioscience and Human-Technology, Agency of Industrial Science and Technology, 1–3, Higashi 1-Chome, Tsukuba city, Ibaragi prefecture, 305–8566, Japan].

EXAMPLE 3

Determination of GlmU Activity

*Corynebacterium glutamicum* LS6/pV11 obtained in Example 2 was cultured according to the method of Example 1, and the culture was centrifuged to obtain wet cells. If desired, the wet cells can be stored at −20° C., and the frozen cells can be thawed before use.

In 0.2 ml of a mixture comprising 100 mmol/l of Tris-HCl (pH 8.0), 10 mmol/l of glucosamine-1-phosphate, 10 mmol/l of acetyl CoA, 10 mmol/l of UTP, 2 mmol/l of $MgCl_2$, 4 g/l of Nymeen S-215 and 10 ml/l of xylene, and 10 g/l of the wet cells, the reaction was conducted at 37° C. for 10 minutes.

After the reaction was carried out, the reaction mixture was analyzed for UDP-GlcNAc formed therein, according to the method described in WO98/12343, and it was confirmed that 7.4 mmol/l of UDP-GlcNAc was produced and accumulated in the reaction mixture. On the other hand, the strain LS6/pC2 containing the vector alone produced 1.2 mmol/l of UDP-GlcNAc.

INDUSTRIAL APPLICABILITY

According to the present invention, mass-scale production of the GlmU polypeptide derived from microorganisms belonging to the genus *Corynebacterium glutamicum* has been enabled by genetic recombinant technology. Using the enzyme, UDP-GlcNAc can be produced efficiently.

---

What is claimed is:

1. An isolated or purified polypeptide comprising the amino acid sequence represented by SEQ ID NO: 1.

2. An isolated or purified DNA coding for the polypeptide of claim 1.

3. An isolated or purified DNA comprising the nucleotide sequence represented by SEQ ID NO:2.

4. A recombinant DNA obtained by ligating the DNA of claim 2 or 3 with a vector.

5. A transformant obtained by introducing the recombinant DNA of claim 4 into a host cell.

6. The transformant of claim 5, wherein the host cell is *Corynebacterium glutamicum*.

7. A process for producing a polypeptide having N-acetylglucosamine-1-phosphate uridyltransferase activity, which comprises culturing the transformant of claim 5 in a medium to produce and accumulate a polypeptide having N-acetylglucosamine-1-phosphate uridyltransferase activity in a culture, and recovering the polypeptide from the culture.

8. A method for producing uridine 5'-diphosphate-N-acetylglucosamine, which comprises
   contacting a culture of the transformant or immobilized cells, of claim 5 with uridine 5'-triphosphate and N-acetylglucosamine phosphate, in an aqueous medium, to produce and accumulate uridine 5'-diphosphate-N-acetylglucosamine in the aqueous medium, and
   recovering the uridine 5'-diphosphate-N-acetylglucosamine from the aqueous medium.

9. The method for producing uridine 5'-diphosphate-N-acetylglucosamine of claim 8, wherein the N-acetylglucosamine phosphate is N-acetylglycosamine-1-phosphate or N-acetylglucosamine-6-phosphate.

10. A method for producing uridine 5'-diphosphate-N-acetylglucosamine, which comprises:
    contacting a cell extract of the transformant of claim 5 or N-acetylglucosamine-1-phosphate uridyltransferase obtained therefrom with uridine 5'-triphosphate, glucosamine phosphate and acetyl coenzyme A, in an aqueous medium to produce and accumulate uridine 5'-diphosphate-N-acetylglucosamine in the aqueous medium, and
    recovering the uridine 5'-diphosphate-N-acetylglucosamine from the aqueous medium.

11. The method for producing uridine 5'-diphosphate-N-acetylglucosamine of claim 10, wherein the glucosamine phosphate is glucosamine-1-phosphate or glucosamine-6-phosphate.

12. An isolated or purified DNA which hybridizes with the DNA of SEQ ID NO. 2 at 65° C. on a filter on which a colony or plaque-derived DNA which is derived from microorganisms belonging to the genus *Corynebacterium* is fixed, in the presence of from 0.7 to 1.0 mol/l NaCl, followed by washing at 65° C. with 0.1×SSC, and which codes for a polypeptide having N-acetylglucosamine-1-phosphate uridyltransferase activity.

13. The DNA of claim 12, wherein the *Corynebacterium* is *Corynebacterium glutamicum*.

14. A recombinant DNA obtained by ligating the DNA of claim 12 with a vector.

15. A transformant obtained by introducing the recombinant DNA of claim 14 into a host cell.

16. The transformant of claim 15, wherein the host cell is *Corynebacterium glutamicum*.

17. A process for producing a polypeptide having N-acetylglucosamine-1-phosphate uridyltransferase activity, which comprises culturing the transformant of claim 15 in a medium to thereby produce and accumulate a polypeptide having N-acetylglucosamine-1-phosphate uridyltransferase activity in a culture, and recovering the polypeptide from the culture.

18. A method for producing uridine 5'-diphosphate-N-acetylglucosamine, which comprises:

contacting a culture of the transformant, or immobilized cells, of claim 15 with uridine 5'-triphosphate and N-acetylglucosamine phosphate, in an aqueous medium, to produce and accumulate uridine 5'-diphosphate-N-acetylglucosamine in the aqueous medium, and recovering the uridine 5'-diphosphate-N-acetylglucosamine from the aqueous medium.

19. The method for producing uridine 5'-diphosphate-N-acetylglucosamine of claim 18, wherein the N-acetylglucosamine phosphate is N-acetylglycosamine-1-phosphate or N-acetylglucosamine-6-phosphate.

20. A method for producing 5'-diphosphate-N-acetylglucosamine, which comprises:

contacting a cell extract of the transformant of claim 15 or N-acetylglucosamine-1-phosphate uridyltransferase obtained therefrom with uridine 5-triphosphate, glucosamine phosphate and acetyl coenzyme A in an aqueous medium to produce and accumulate uridine 5'-diphosphate-N-acetylglucosamine in the aqueous medium, and recovering the uridine 5'-diphosphate-N-acetylglucosamine from the aqueous medium.

21. The method for producing uridine 5'-diphosphate-N-acetylglucosamine of claim 20, wherein the glucosamine phosphate is glucosamine-1-phosphate or glucosamine-6-phosphate.

22. *Corynebacterium glutamicum* LS6/PV11 (FERM BP-6937).

\* \* \* \* \*

SEQUENCE LISTING

```
<160> NUMBER OF SEQ ID NOS: 2

<210> SEQ ID NO 1
<211> LENGTH: 485
<212> TYPE: PRT
<213> ORGANISM: Corynebacterium glutamicum ATCC13032

<400> SEQUENCE: 1

Met Ser Ala Ser Asp Phe Ser Ser Ala Val Val Val Leu Ala Ala Gly
 1               5                  10                  15

Ala Gly Thr Arg Met Lys Ser Asp Leu Gln Lys Thr Leu His Ser Ile
            20                  25                  30

Gly Gly Arg Ser Leu Ile Ser His Ser Leu His Ala Ala Ala Gly Leu
        35                  40                  45

Asn Pro Glu His Ile Val Ala Val Ile Gly His Gly Arg Asp Gln Val
    50                  55                  60

Gly Pro Ala Val Ala Gln Val Ala Glu Glu Leu Asp Arg Glu Val Leu
65                  70                  75                  80

Ile Ala Ile Gln Glu Glu Gln Asn Gly Thr Gly His Ala Val Gln Cys
                85                  90                  95

Ala Met Asp Gln Leu Glu Gly Phe Glu Gly Thr Ile Ile Val Thr Asn
            100                 105                 110

Gly Asp Val Pro Leu Leu Thr Asp His Thr Leu Ser Ala Leu Leu Asp
        115                 120                 125

Ala His Val Glu Val Pro Thr Ala Val Thr Val Leu Thr Met Arg Leu
    130                 135                 140

Asp Asp Pro Thr Gly Tyr Gly Arg Ile Val Arg Asn Glu Glu Gly Glu
145                 150                 155                 160

Val Thr Ala Ile Val Glu Gln Lys Asp Ala Ser Ala Glu Val Gln Ala
                165                 170                 175

Ile Asp Glu Val Asn Ser Gly Val Phe Ala Phe Asp Ala Ala Ile Leu
            180                 185                 190
```

```
Arg Ser Ala Leu Ala Glu Leu Lys Ser Asp Asn Ala Gln Gly Glu Leu
            195                 200                 205

Tyr Leu Thr Asp Val Leu Gly Ile Ala Arg Gly Glu Gly His Pro Val
        210                 215                 220

Arg Ala His Thr Ala Ala Asp Ala Arg Glu Leu Ala Gly Val Asn Asp
225                 230                 235                 240

Arg Val Gln Leu Ala Glu Ala Gly Ala Glu Leu Asn Arg Arg Thr Val
                245                 250                 255

Ile Ala Ala Met Arg Gly Gly Ala Thr Ile Val Asp Pro Ala Thr Thr
                260                 265                 270

Trp Ile Asp Val Glu Val Ser Ile Gly Arg Asp Val Ile Ile His Pro
            275                 280                 285

Gly Thr Gln Leu Lys Gly Glu Thr Val Ile Gly Asp Arg Val Glu Val
        290                 295                 300

Gly Pro Asp Thr Thr Leu Thr Asn Met Thr Ile Gly Asp Gly Ala Ser
305                 310                 315                 320

Val Ile Arg Thr His Gly Phe Asp Ser Thr Ile Gly Glu Asn Ala Thr
                325                 330                 335

Val Gly Pro Phe Thr Tyr Ile Arg Pro Gly Thr Thr Leu Gly Pro Glu
                340                 345                 350

Gly Lys Leu Gly Gly Phe Val Glu Thr Lys Lys Ala Thr Ile Gly Arg
            355                 360                 365

Gly Ser Lys Val Pro His Leu Thr Tyr Val Gly Asp Ala Thr Ile Gly
        370                 375                 380

Glu Glu Ser Asn Ile Gly Ala Ser Ser Val Phe Val Asn Tyr Asp Gly
385                 390                 395                 400

Glu Asn Lys His His Thr Thr Ile Gly Ser His Val Arg Thr Gly Ser
                405                 410                 415

Asp Thr Met Phe Ile Ala Pro Val Thr Val Gly Asp Gly Ala Tyr Ser
                420                 425                 430

Gly Ala Gly Thr Val Ile Lys Asp Asp Val Pro Pro Gly Ala Leu Arg
            435                 440                 445

Val Ser Gly Gly Arg Gln Arg Asn Ile Glu Gly Trp Val Gln Lys Lys
        450                 455                 460

Arg Pro Gly Thr Ala Ala Ala Gln Ala Ala Glu Ala Ala Gln Asn Val
465                 470                 475                 480

His Asn Gln Glu Gly
            485

<210> SEQ ID NO 2
<211> LENGTH: 1455
<212> TYPE: DNA
<213> ORGANISM: Corynebacterium glutamicum ATCC13032

<400> SEQUENCE: 2
ttgagcgcaa gcgatttctc gagcgcagtt gtcgttttgg cagctggtgc cggaacccga      60
atgaaatcag acttacaaaa aacgttgcat agcatcggtg gacgcagtct catttcacat     120
agcttgcatg cagctgccgg gcttaatccc gagcacattg ttgcagtaat tggacatgga     180
cgcgaccagg tgggtccagc cgttgcccag gttgcagaag aactggaccg ggaagtcctc     240
atcgctatcc aagaggaaca aaatggcacg gacacgctg tgcagtgcgc catggatcag     300
ctcgagggct tgaaggcac gatcattgtc accaacggcg atgttcccct gctcaccgac     360
cacactctgt ctgcactgct ggatgcacac gtggaagttc caaccgctgt caccgtgttg     420
```

```
                                                                -continued accatgcgtc tggatgaccc caccggctac ggccgcatcg tgcgcaacga agaaggcgaa    480
gtcaccgcca tcgttgagca aaaagatgct tcagcagaag tccaagccat cgatgaggtc    540
aactccggtg tctttgcttt cgacgccgcc atcttgcgtt ccgcactggc tgaactgaag    600
tccgacaacg ctcagggcga gctgtacctg accgacgtat tgggcattgc tcgtggcgag    660
ggccacccag tgcgcgccca caccgccgcc gatgctcgtg aactcgccgg tgtcaacgat    720
cgtgtgcagc tcgcagaagc cggcgccgaa ctaaaccgtc gcaccgtcat cgccgctatg    780
cgtggtggcg caaccatcgt tgatccagca accacctgga tcgatgtgga ggtttctatc    840
ggccgcgacg tgatcatcca ccctggcacc cagctcaagg gcgaaactgt catcggagac    900
cgcgttgaag ttggtccaga caccaccttg accaacatga ccatcggcga cggcgcatcc    960
gtaatccgca cccacggttt cgactccacc atcggtgaaa acgccaccgt tggcccttc    1020 acctacatcc gcccaggaac cacactggga ccagaaggca agctcggtgg cttcgtagaa   1080
accaagaagg ccacaatcgg ccgtggctcc aaggttccac acctcaccta tgtcggcgac   1140
gccaccatcg gcgaggaatc caacatcgga gcctcctctg tcttcgtgaa ctacgacggt   1200
gaaaacaagc accacaccac catcggcagc cacgttcgca ctggttctga caccatgttt   1260
atcgctccag tgaccgtggg tgacggagcg tattccggag ccggtacagt aattaaagac   1320
gatgttccgc caggagccct tcgcgtgtcc ggcggacgcc aacgaaacat cgaaggctgg   1380
gtgcaaaaga agcgccctgg aaccgctgca gcacaagccg cagaagccgc ccaaaacgtc   1440
cacaaccagg aaggc                                                    1455
```